United States Patent [19]

Gawrisch et al.

[11] Patent Number: 4,909,630
[45] Date of Patent: Mar. 20, 1990

[54] METHOD AND DEVICE FOR DETERMINING THE CHANGE IN THICKNESS AND/OR ORIENTATION WITHIN A STRIP OF OPTICALLY ACTIVE MATERIAL

[75] Inventors: Wolfgang Gawrisch, Gau-Bischofsheim; Thomas Trzebiatowski, Wiesbaden, both of Fed. Rep. of Germany

[73] Assignee: Hoechst Aktiengesellschaft, Frankfurt am Main, Fed. Rep. of Germany

[21] Appl. No.: 939,111

[22] Filed: Dec. 8, 1986

[30] Foreign Application Priority Data

Dec. 11, 1985 [DE] Fed. Rep. of Germany ....... 3543632

[51] Int. Cl.⁴ .............................................. B29C 55/12
[52] U.S. Cl. ..................................... 356/364; 264/40.2
[58] Field of Search ................ 356/382, 364, 366, 367, 356/35, 33, 365, 368, 369; 264/40.2, 40.7

[56] References Cited

U.S. PATENT DOCUMENTS

| | | | |
|---|---|---|---|
| 3,124,637 | 3/1964 | Heitzer | 356/35 |
| 3,183,763 | 5/1965 | Kuester | 356/33 |
| 3,421,820 | 1/1969 | Huebschman | 356/365 |
| 3,446,977 | 5/1969 | Bateson | 356/367 X |
| 3,466,129 | 9/1969 | Agatsuma et al. | 356/365 |
| 3,871,771 | 3/1975 | Scott | 356/364 |
| 4,584,476 | 4/1986 | Colombotto et al. | 356/35 X |
| 4,684,487 | 8/1987 | Gawrisch | 356/364 X |

FOREIGN PATENT DOCUMENTS

2836245 3/1979 Fed. Rep. of Germany.
2338305 6/1979 Fed. Rep. of Germany.
3106818 9/1982 Fed. Rep. of Germany.

OTHER PUBLICATIONS

Trubnyakov et al, "Equipment for Continuously Monitoring the Quality of Film Materials", Meas. Tech, vol. 21, No. 9 (Sep. 1978).
Foppl, Monch "Praktische Spannungsoptik", Berlin 1972, Springer-Verlan, S. 6–17, pp. 192–196.

Primary Examiner—Richard A. Rosenberger
Attorney, Agent, or Firm—Foley & Lardner, Schwartz, Jeffery, Schwaab, Mack, Blumenthal & Evans

[57] ABSTRACT

An interference image of a biaxially stretched film strip 4 is generated optically. Streaks in the film strip are areas of different orientation and/or thickness d which are distinguished from the streakfree areas in the interference image by clearly different intensities. In order to generate the interference image, a light-source 1, a diffuser screen 2 and a polarizer 3 are arranged on one side of the film strip 4, and an analyzer 5 and a filter 6 are arranged on the other side of the film strip 4. The light beam of the light source 1 is polarized by the polarized 3 and, within the film (whose main refractive indices $n_1$ and $n_2$ have an angle of 45° or 135° respectively to the polarization plane) is split into two beams, oscillating perpendicularly to one another, which have a path difference $\Gamma = (n_1 - n_2)d$ after emerging from the film. Of the light behind the film, in general elliptically polarized, only that portion of the light which oscillates parallel to the analyzer plane, which is perpendicular to the polarization plane, passes through the analyzer 5. In general, a colored interference image is obtained if the light source emits polychromatic light. A detector 7 as light-sensitive element, e.g. a video camera, comprising a light-sensitive diode matrix, which is connected to an image analysis and computing unit 8 for evaluation of the interference image, is arranged behind the filter, which serves to increase the contrast of the image.

15 Claims, 7 Drawing Sheets

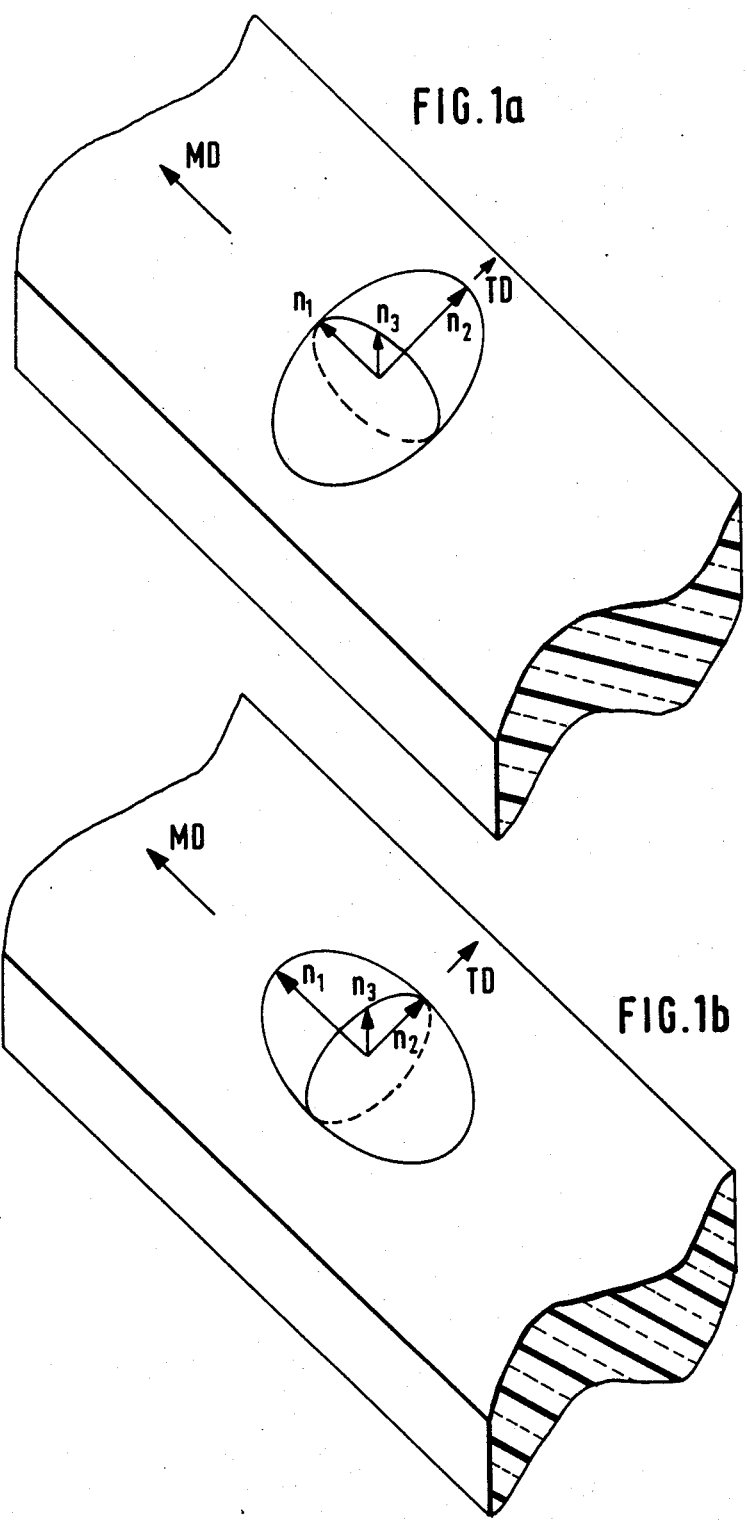

METHOD AND DEVICE FOR DETERMINING THE CHANGE IN THICKNESS AND/OR ORIENTATION WITHIN A STRIP OF OPTICALLY ACTIVE MATERIAL

BACKGROUND OF THE INVENTION

The invention relates to a method and device for determining the change in thickness and/or orientation within a strip of optically active material by measuring the intensity of light shining through the strip of material.

In the production of films from thermoplastic materials, polymer granulate is formed into a molten film by means of an extruder and a slit die. This film solidifies on contact with chill rolls to form a precursor film, which is then stretched in steps or simultaneously by means of stretching machines. During the stretching process, the molecule chains in the film material are oriented, which is essentially caused by the stretching process. The stretching process is carried out initially in or transverse to the machine direction (longitudinal or transverse stretching, respectively) and subsequently in the direction that the film was not initially stretched (transverse or longitudinal stretching, respectively). The transverse stretching is generally carried out in a frame. After completion of the stretching, the film strip is subjected to temperature treatment, by means of which the aligned molecule chains in the film are thermally fixed; the shape of the film material is thus maintained. A partially crystalline film, preferably biaxially oriented, is obtained through the fixing.

The orientation within the film can be described by the index ellipsoid (indicatrix), which is defined by the refractive indices $n_1$, $n_2$ and $n_3$. Different refractive indices in three axial directions perpendicular to one another result in a correspondence to the orientation of the molecule chains in the film. The refractive index which is parallel to the machine direction is designated $n_1$, the index at 90° with respect to the machine direction and in the film plane is designated $n_2$, and the index in the direction perpendicular to the film plane is designated $n_3$. If a biaxially oriented film is introduced into a polarization arrangement, the polychromic or white light of a light source, after passing through the polarization arrangement, gives a characteristic interference color and intensity corresponding to the thickness and orientation of the molecule chains of the film web.

From German Patent No. 2,338,305, a method is known for the determination of the linear birefringence of an optically active material, in which the material is transilluminated with linearly polarized light and the light emerging in a polarization plane perpendicular to the polarization plane of the incident light is detected, at least one wavelength being determined at which the detected light is extinguished. The measuring device used for this comprises a light source whose beam transilluminates a polarizer in which the required linearly polarized wave is formed. This wave then passes through the film to be measured and reaches an analyzer. From there, the wave passes into a detector system. The detector system may be designed as a prism or grating, or as an optical multichannel analyzer having a large number of detectors. The light source emits monochromatic or white light.

From German Offenlegungsschrift No. 3,106,818, a method is known for the continuous determination of multiaxial orientation conditions of stretched films or sheets via their main birefringence values, in which three laser beams, generated by three lasers or by splitting one laser beam into three sub-beams, are used. One beam passes vertically through the film and the other two pass through it inclined at such an angle that the planes of inclination are perpendicular to the film plane and contain the two main orientation directions. The phase differences of the laser beam intensities are measured continuously after the beams pass through the film using a quarter-wave plate and a rotating analyzer. The three main birefringence values of the film are determined continually from the three phase differences, taking into account the two angles of inclination of the inclined laser beams and the film thickness measured in another fashion. The measuring device comprises three lasers whose beams are aligned parallel to each other by a suitable lens or mirror arrangement after passing through the film. The light beam of the first laser is incident perpendicularly on the film plane, while the light beams of the two other lasers are incident on the film at an angle $\Phi$ with respect to the film normals. The light beam of the first laser proceeds in a plane which contains the film normals and the main stretching direction of the film, while the laser beam of the other laser is in a plane which is determined by the film normals and the transverse stretching direction of the film. The light beams, initially linearly polarized, proceeding from the lasers are elliptically polarized by the optical anisotropy of the stretched film. A quarter-wave plate below the film converts the elliptical polarization of the three laser beams into linear polarization. A rotating polarizing filter below the quarter-wave plate extinguishes the beams if their polarization directions are perpendicular to the polarization direction of the polarizing filter. The intensities of the laser beams are converted by light-sensitive detectors into periodical electrical signals which are phase-displaced to one another. This phase displacement can be determined using two phase meters, the third phase displacement making the other two add up to 0°. The birefringence values can be determined from the measured phase displacements using a computer and used directly as measured quantities for the biaxial film orientation for control of the film-stretching equipment.

This known measuring device is instrumentally complicated due to the fact that it uses three lasers or an optical system to split a single laser beam into three sub-beams.

If the film has areas in which the orientation of the molecule chains in or transversely to the machine direction or the thickness are different compared to the surrounding areas, $n_1$, $n_2$, or the film thickness $d$ changes, and another path difference $\Gamma = (n_1 - n_2)d$ results in these areas. An alteration of the interference color and the intensity is connected with this.

Areas of lesser or greater orientation in the film can be produced as a result of localized thick or thin points in the precursor film. These areas are deformed to an essentially lesser or greater extent during the stretching process. If the thick or thin points in the precursor film have the shape of a streak several millimeters in width and up to several meters in length, the film resulting from the stretching process will also have streak areas of lesser or greater orientation with a width of several millimeters and a length of several meters. The mechanical properties (E module, $\sigma_5$-value) of the film correlate to the orientation. Streaks having lesser or greater orientation thus also exhibit lesser or greater mechanical properties. The appearance of such streaks thus leads to a reduction in quality of the film, which must be detected quickly.

SUMMARY OF THE INVENTION

The present invention has the object of creating a method and a device which make it possible to continuously detect the changes in thickness and/or orientation in certain areas of a strip of optically active material compared to the surrounding strip of material, and to assign these changes clearly to the location in the strip of material.

This object is achieved according to the invention by transilluminating the strip of material passing between crossed polarizers with polychromatic light and by imaging, on a light-sensitive detector, the portion of the polarized light whose oscillation direction is parallel to the direction of the polarization plane of an analyzer; this light is then subjected to an intensity analysis and reproduced several times within a pre-specified time span.

In a development of the method, the polarized light proceeding parallel to the oscillation direction of the polarization plane of the analyzer is recorded and plotted as a function of the location on the strip of material, thereby recording the width of the strip of material and the distance through which it has moved. For this purpose, a pre-selectable threshold value is set for the intensity analysis of the optical signals converted into electrical signals by the detector, and differences from the threshold value show the distinction between an unchanged strip of material and a strip of material which is changed in thickness and/or orientation. The pre-specified time span for the multiple reproduction of the intensity analysis is 0.01 millisecond to 1 second. The transillumination of the strip of material and the determination of changes in thickness and/or orientation is carried out continuously during running production of the strip of material. According to the method of the present invention, the process control of the speed, the heating, and the longitudinal and transverse stretching of the strip of material are carried out using the continuously determined intensity analysis data.

The device for carrying out the method is distinguished in that a polarizer and an analyzer, crossed with respect to one another, are located above and below the strip of material in the ray path of a light source to a detector. The detector is connected to an image analysis and computing unit for the intensity analysis of the image of the strip of material received by the detector. The analyzed image of the image analysis and computing unit is fed to a monitor for reproduction and an output unit for recording.

In the device, the interference image of the strip of material, e.g. a strip of film, which is preferably stretched biaxially and which is fed between two crossed polarizers is fed, via the light-sensitive detector, to the computing unit, which carries out an evaluation of the brightness values using the integrated image analysis system. In addition, data on the width and running speed of the film are transferred to the computing unit, so that it is possible to assign the streaks to locations on the film strip and so that this assignment may be recorded and plotted by the output unit.

The generation of the interference image and the determination of the location of streaks is carried out during running production of the film strip, i.e. the invention makes on-line control of the biaxially stretched film strip possible.

The polychromatic (white), polarized light shining through the film strip is split into two polarized waves perpendicular to one another. After passing through the film strip, the two waves generally combine to form an elliptically polarized wave, of which the portion polarized parallel to the analyzer direction is allowed to pass through the analyzer, and the intensity of which is measured in such a fashion that the image behind the analyzer is recorded as a raster image by the detector, e.g. a video camera. The contrast is evaluated by the computer for the determination of those areas of the same intensity which differ markedly from the intensity of the streak-free area of the film strip.

The device comprises the light source, the imaging device for transillumination of the film, and the light-sensitive detector for measuring the intensity of the light passing through the film strip. A diffuser screen serves to even out the light and a filter serves to increase the contrast. The polarizer is, for example, a dichroic foil and the analyzer is a polarizing prism of birefringent crystals or, likewise, a dichroic foil in the form of a polarizing filter. The light-sensitive detector is a video camera which supplies a raster image, and the computing unit determines areas of the same light intensity and thus the profile for the contrast evaluation of the raster image. If the light intensity in certain areas is above a certain prespecified threshold value, these areas are recorded as streaks and output, via the output unit, in such a fashion that allocation to locations on the film strip is possible.

With the present invention, the advantage is achieved that streaks, i.e. areas of relatively little or relatively great orientation or thickness, are detected during the running production process.

BRIEF DESCRIPTION OF THE DRAWINGS

The invention is described in greater detail below with reference to the drawings, in which:

FIGS. 1a and 1b show, schematically, the position of the index ellipsoid of the refractive index in different biaxially oriented films;

DETAILED DESCRIPTION OF PREFERRED EMBODIMENTS

Figure 2A:
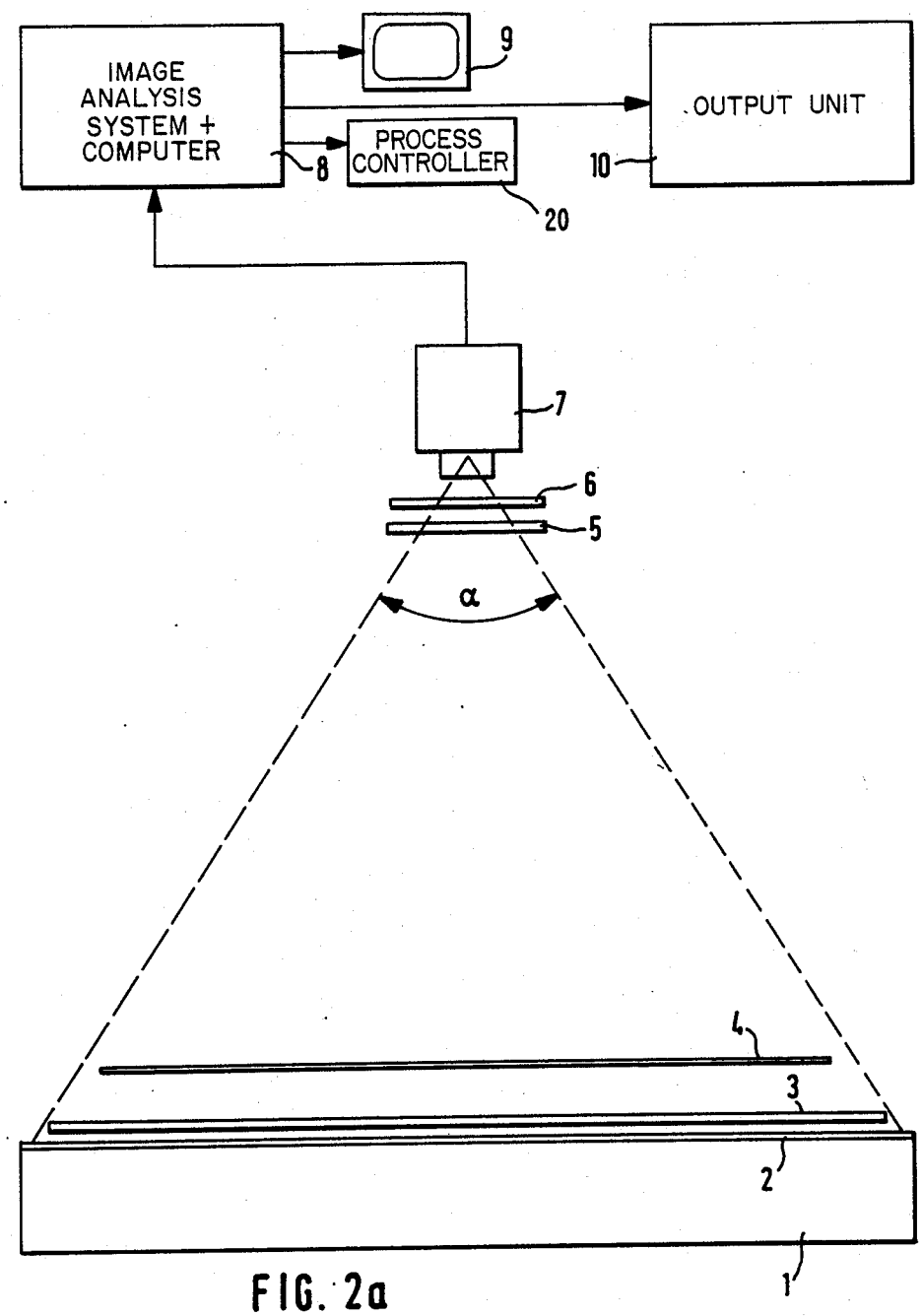
FIGS. 2a and 2b show, schematically, a side view and a plan view of the device according to the invention.

In FIGS. 1a and 1b, the ideal anisotropy conditions—aimed at in practice—of a biaxially stretched film strip are represented, with reference to the index ellipsoid, for a longitudinal/transverse stretching and a transverse/longitudinal stretching process. As FIG. 1a shows, different orientation conditions generally occur, caused by the method parameters, in the longitudinal or machine direction MD and in the transverse direction TD. In the case of a production process in which the film is first stretched longitudinally and then transversely, the machine direction MD and the main orientation direction with the greatest refractive index $n_2$ are perpendicular to one another in the film center, as shown by FIG. 1a. In a production process in which the film strip is initially stretched transversely and then longitudinally, the machine direction MD and the main orientation direction of the greatest refractive index $n_1$ are aligned parallel to one another.

The basic construction of a measuring device for the detection of streaks in a moving strip of optically active material 4, e.g. a film strip of polyethylene terephthalate, is described with reference to FIGS. 2a and 2b.

The polarizing arrangement, comprising a polychromatic, i.e. a white light source a polarizer 3, an analyzer 5, whose polarization plane is rotated by 90° to that of the polarizer 3, and a light-sensitive detector 7, is arranged on both sides of a strip of material 4. The machine direction MD, and thus the direction of the refractive index $n_1$, forms an angle of 45° both with the polarization plane of the polarizer 3 and with the analyzer 5, as shown by FIG. 2b. Light which is linearly polarized in the direction of the polarizer 3 is then divided in the strip of material 4 into two equally strong waves, polarized in the directions of the refractive indices $n_1$ and $n_2$, which pass through the strip of material 4 with different velocities of propagation and thus emerge from the film strip at different times. This results in a path difference $\Gamma=(n_1-n_2)d$, where d is the film thickness. The two light waves combine behind the film strip to form a generally elliptically polarized wave, of which only that part whose oscillation direction is parallel to the direction of the polarization plane of the analyzer 5 is allowed to pass through the analyzer 5.

The rays of the polychromatic light source 1 are evened out by a diffuser screen 2, linearly polarized by the polarizer 3 in such a fashion that the direction of the polarization plane has an angle of 45° to the machine direction MD. The polarized light is split in the film strip 4 into two beams which are perpendicular to one another and which are parallel to the directions of the refractive indices $n_1$ and $n_2$. The part of the elliptically polarized light whose oscillation direction is parallel to the polarization plane of the analyzer 5, which is rotated by 90° to the polarization plane of the polarizer 3, is allowed to pass through the latter. It then passes through a filter 6 to increase the contrast and reaches the light-sensitive detector 7, for example a video camera having a two-dimensional diode matrix as light-sensitive element. The optically visible image is evaluated point-by-point with respect to its brightness by a special image analysis and computing unit 8. An intensity analysis is carried out in the image analysis and computing unit 8 with the aid of a selectable threshold value setting for the electrical signals which the light-sensitive detector 7 supplies based on the optical signals received. Subsequently, the binary image obtained is imaged on the screen of a monitor 9, which is connected to the image analysis and computing unit 8. The data output by the unit 8 are, furthermore, transferred to an output unit 10, registered in this unit, and recorded. This output unit 10 can be, for example, a dot matrix printer, an x/y recorder or a similar recording unit. The output data may also serve as an input to a process controller 20 for continuous process control of the speed, the heating, the longitudinal and transverse stretching and other process parameters in the production of the film strip 4.

Figure 3:
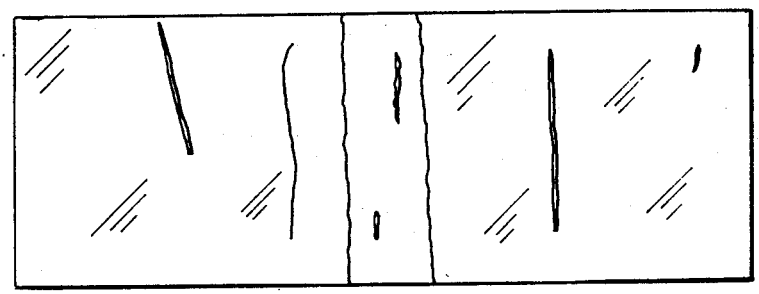
FIG. 3 shows an optical interference image of a polyethylene terephthalate (PET) film with streaks.

An optical interference image of a PET film having a streak is represented schematically in FIG. 3.

Figure 4A:
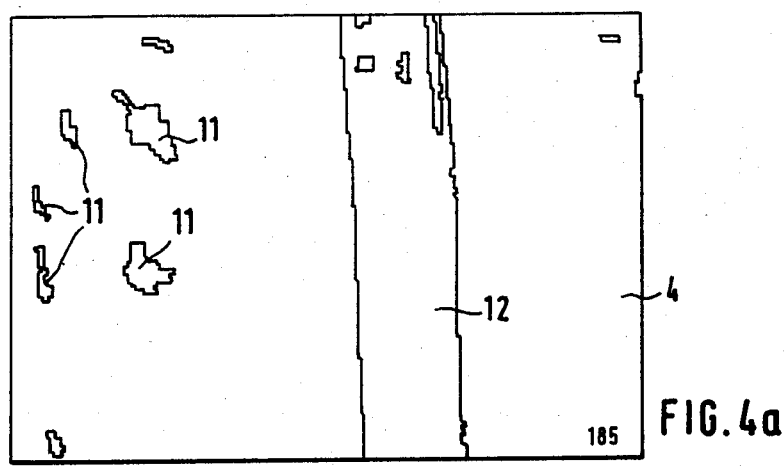
FIGS. 4a through 4c show monitor images, recorded using a video camera, of a polyethylene terephthalate (PET) film with streaks, where images have been converted in the image analysis and computing unit at various threshold value settings.
Figure 4B:
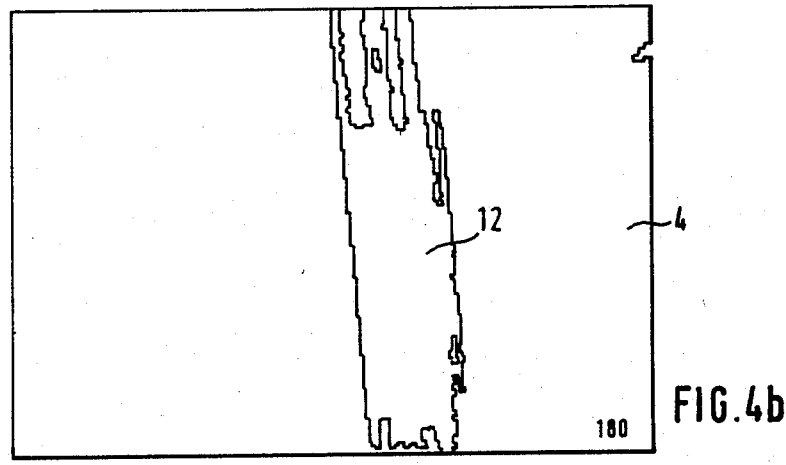
Figure 4C:
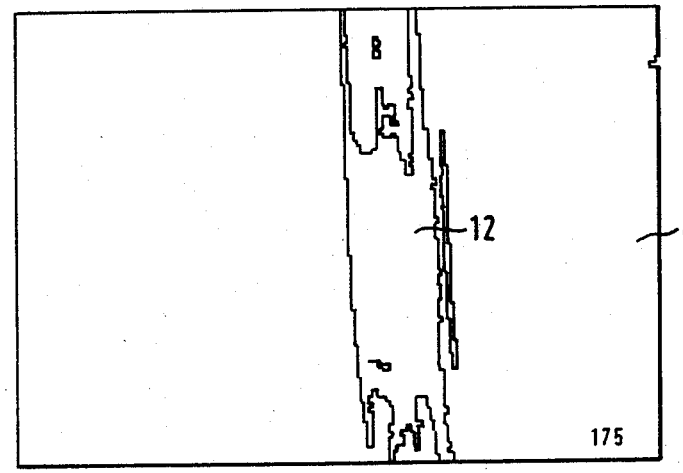

FIGS. 4a to 4c show binary images of streaks in a stationary film strip 4 analyzed using the image analysis and computing unit 8. The binary images were imaged on the monitor 9 with decreasing threshold values, i.e. increasing light intensity. The discriminator setting in the image analysis and computing unit 8 was reduced during the recording from a scale value of 185 to a scale value of 175 in steps of 5 scale divisions. It can be seen that the streak 12 in FIGS. 4b and 4c can be clearly distinguished from the individual inclusions 11, shown in FIG. 4a, which have orientations other than that of the surrounding film strip 4.

Figure 5:
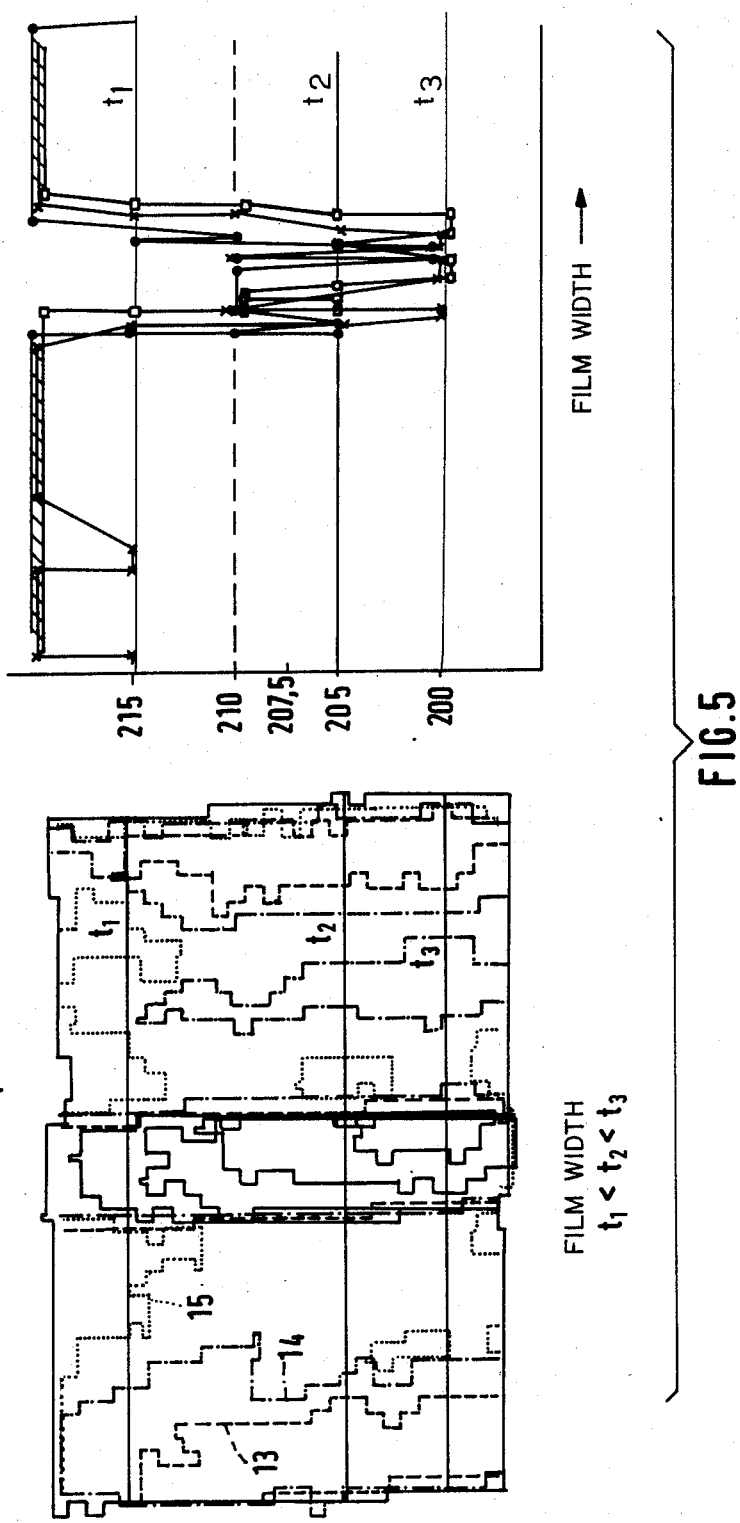
FIG. 5 shows a schematic diagram of the light intensity of an image of a stationary polyethylene terephthalate (PET) film with streaks, recorded at different threshold value settings and at different times.

The left-hand picture in FIG. 5 shows binary images on the screen of the monitor 9 of a streak at various threshold values or settings in the case of a stationary film strip 4, the dashed line 13 corresponding, for example, to a threshold setting of 205, the dot-dashed line 14 corresponding to a setting of 210, and the dotted line 15 corresponding to a threshold setting of 215 in the image analysis and computing unit 8. Furthermore, time lines $t_1$, $t_2$ and $t_3$ are entered perpendicular to the movement or machine direction MD, $t_1$ being less than $t_2$ and $t_2$ being less than $t_3$ for the corresponding times. In the case of a certain strip speed of the film strip 4 the time interval $t_2-t_1$ or $t_3-t_2$ can range from 0.01 msec to 1.0 sec, possibly even up to 2.0 sec.

Figure 6:
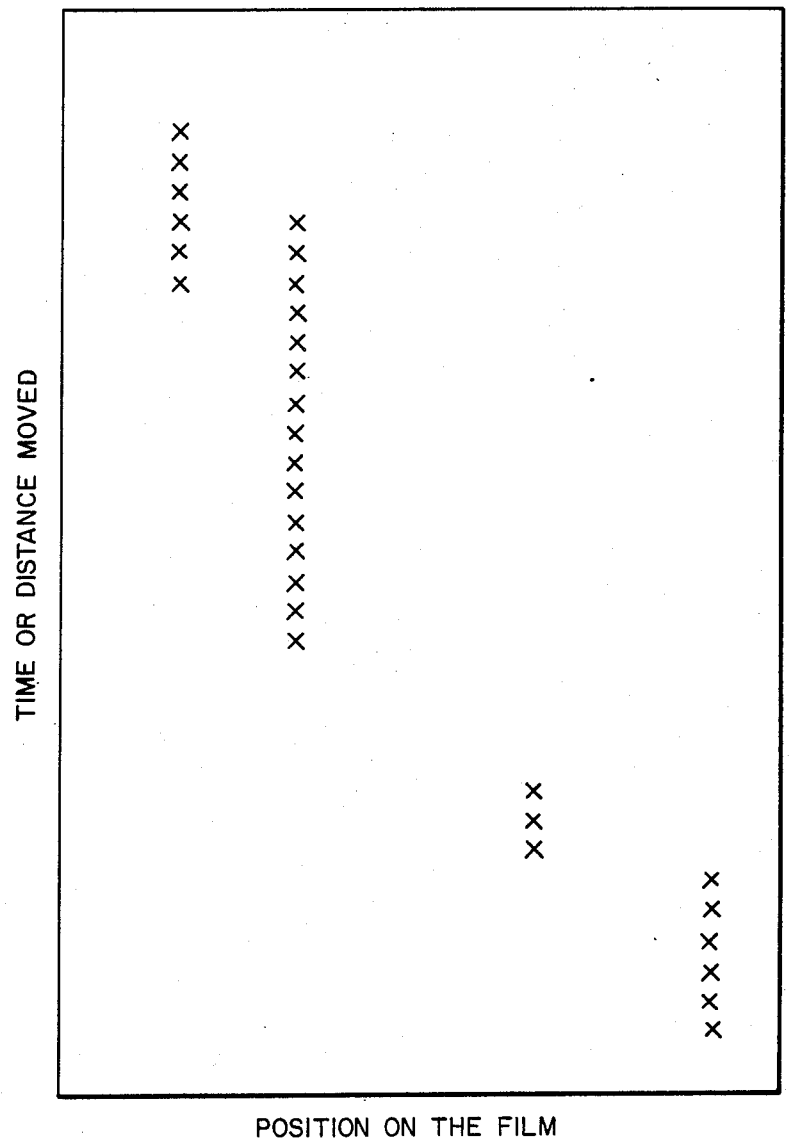
FIG. 6 shows a schematic diagram of a print-out from the output unit.

In the right-hand picture in FIG. 5, the intensity profile along the time lines $t_1$, $t_2$ and $t_3$ is represented perpendicular to the direction of movement, and thus to the streak direction, in binary images having different threshold values. As can be seen, the streak can be distinguished by a higher intensity, i.e. a lower threshold value compared to the surrounding film strip 4. The inclusions 11, indicated by crosses, along the time line $t_1$ in the right-hand picture of FIG. 5 can be excluded from the binary images by pre-specifying a suitable threshold value and observing this value over a certain pre-selectable time span as a function of the location. If this threshold value is continually exceeded at the same location during the prespecified time span then the crosses indicate a streak, otherwise they indicate inclusions. In the latter case, the threshold value is reduced until these inclusions no longer appear in the binary image. As can be seen from the right-hand picture of FIG. 5, the inclusions 11 in FIG. 4a and the streak along the time line $t_1$, are clearly distinguished from one another, as can be seen at a threshold value of 215. At a threshold value of 210, the inclusions are eliminated from the binary images. At a threshold value setting of 205, even the fine structure of the film strip 4 can be seen along the time line $t_2$, meaning that differentiation between the streak and the surrounding film strip 4 becomes difficult. In this case, it is appropriate to set the threshold value setting to a value greater than 205 and less than 215, for example to a value of 210 or 207.5. The positions of increased light intensity compared to the surrounding film strip are marked by a cross in FIG. 6. The time or the distance through which the film strip 4 has moved are recorded in the ordinate direction and the respective position on the film strip 4 is recorded in the abscissa direction.

Figure 2B:
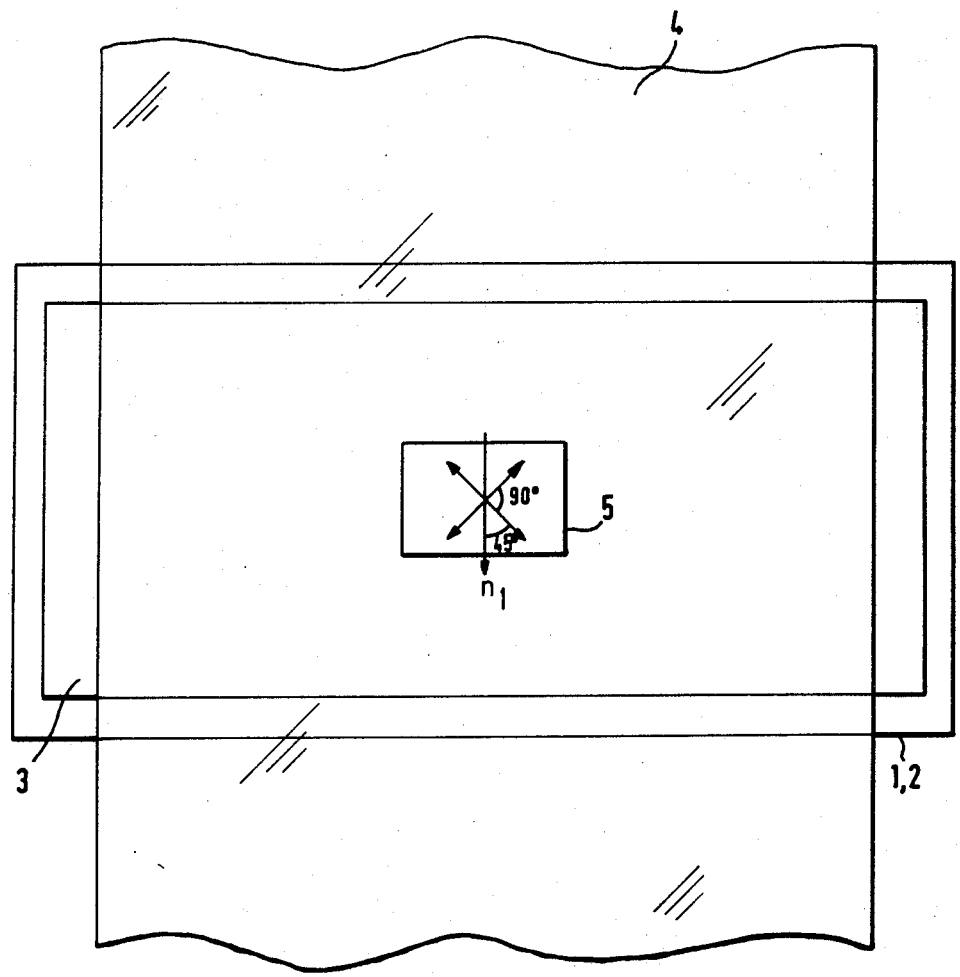

In order to be able to suppress more easily interferences caused by slight intensity variations of the background, which correspond to the streak-free film areas, the filter 6 shown in FIG. 2a is used to increase the contrast.

Figure 7:
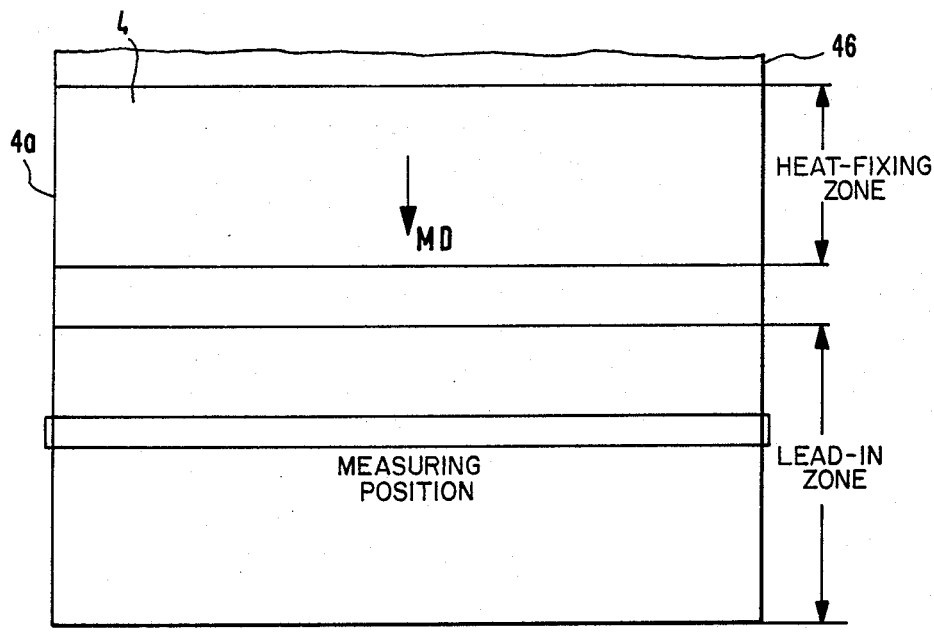
FIG. 7 shows a schematic diagram of a plan view of the measuring position of the film.

FIG. 7 shows a schematic representation of a plan view of the measuring position of the detector 7 or of the video camera in the lead-in zone to the spooling of the film strip 4. The lead-in zone is located after the thermal fixing zone in the movement or machine direction MD. The measuring position or the image field of the video camera extends beyond the width of the film strip 4. This makes it possible to specify accurately the location of the streak via the film width, since the elliptically polarized light is extinguished at the edges 4a and 4b of the film strip 4. In this respect, reference is made to FIG. 2a, from which it can also be seen that the image field of the video camera is greater than the width of the film strip 4, since the cone (dashed line) of the aperture angle α of the video camera lens passes the edges of the film strip 4 at a certain distance. Since the polarizer 3 and the analyzer 5, crossed with respect to each other, cover at least the image field of the video camera, areas of complete darkness result on the left and right of the edges 4a and 4b, respectively, of the film strip 4. As a result of the crossed position of the polarizer 3 and analyzer 5, i.e. when passing over the edges of the film strip 4, the light intensity across the width of the strip 4 is great as a result of the extinction which occurs. Precise control of the width of the film strip 4 and exact determination of the location of streaks occurring in the film strip 4 are thus possible.

Figure 8:
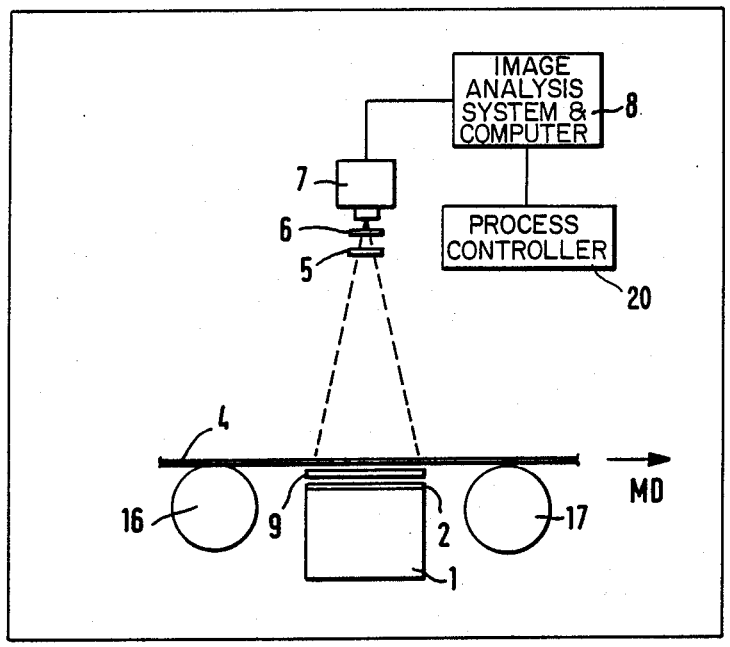
FIG. 8 shows schematically a design of a device for determining streaks of oriented polyethylene films in the on-line production.

FIG. 8 shows a schematic view of the location of the attachment of the polarization arrangement and measuring device for continuous detection of streaks in a production plant between rolls 16 and 17 of the lead-in zone before spooling of the stretched film strip 4.

What is claimed is:

1. A method for determining changes in thickness and molecule chain orientation within a strip of optically active material, comprising the steps of:
   (a) passing a strip of optically active material between at least one pair of crossed polarizers;
   (b) transilluminating at least a portion of the strip between the crossed polarizers with polychromatic light whereby the light, after passing through the strip and the crossed polarizers, is polarized;
   (c) imaging said portion of the transilluminated strip onto a light-sensitive detector including a two dimensional array of imaging elements;
   (d) subjecting said imaged portion of the transilluminated strip to an intensity analysis several times within a pre-specified time period; and
   (e) setting a pre-selectable threshold value for the intensity analysis of said imaged portion of the transilluminated strip.

2. The method as claimed in claim 1, further including the step of recording the intensity of the portion of the transilluminated strip as a function of the width of the strip, wherein the intensity is indicative of changes in thickness and molecule chain orientation in the strip.

3. The method as claimed in claim 1, further including the step of moving the strip between the at least one pair of polarizers.

4. The method as claimed in claim 1, further including the steps of recording the intensity of the portion of the transilluminated strip as a function of the width of the strip and the distance through which the strip has moved.

5. The method as claimed in claim 1, further including the step of continuously controlling process operations performed on the strip as it is moved in response to the changes in thickness and molecule chain orientation, wherein the process operations include adjusting the speed, heating, and longitudinal and transverse stretching of the strip.

6. A method for determining changes in thickness and molecule chain orientation within a strip of optically active material, comprising the steps of:
   (a) providing a strip of optically active material between at least one pair of crossed polarizers;
   (b) transilluminating at least a portion of the strip between the crossed polarizers with polychromatic light whereby the light, after passing through the strip and the crossed polarizers, is polarized; and
   (c) measuring the intensity of the transilluminated strip wherein the intensity is indicative of the changes in thickness and molecule chain orientation in the strip, said measuring step comprising the steps of:
   imaging, on a light sensitive detector including a two dimensional array of imaging elements, a portion of the portion of the transilluminated strip;
   converting said imaged portion of transilluminated strip into electrical signals;
   setting a threshold value indicative of a material that is unchanged with respect to thickness and molecule chain orientation; and
   subtracting the electrical signals from the threshold value to obtain differences, wherein the differences are indicative of changes in thickness and molecule chain orientation as a function of the width of the strip.

7. A device for determining changes in thickness and molecule chain orientation within a strip of optically active material, comprising:
   a first polarizing means;
   a second polarizing means crossed with respect to said first polarizing means, wherein said first and second polarizing means are arranged on either side of the planar area of the strip of optically active material moved between the first and second polarizing means, and in the ray path of a polychromatic light source transilluminating at least a portion of the strip whereby the light, after passing through said first and second polarizing means and the strip, is polarized;
   measuring means for measuring and analyzing the intensity of the transilluminated strip to determine changes in thickness and molecule chain orientation within the portion of the transilluminated strip, wherein said measuring means includes a light sensitive detector comprising a two dimensional array of imaging elements; and
   means for recording the changes in thickness and molecule chain orientation as a function of the width of the strip.

8. The device as claimed in claim 7, further including a means for moving the strip in a direction between said first and second polarizers, said recording means further recording the changes as a function of the distance through which the strip has moved.

9. The device as claimed in claim 8, wherein the first and second polarizing means are arranged to have their respective planes of polarization oriented at an angle of 90° with respect to each other and to further have their respective planes of polarization orientated at an angle of 45° with respect to the movement direction of the strip.

10. The device as claimed in claim 8, further including means for continuously controlling process operations performed on the strip as it is moved in response to the changes in thickness and molecule chain orientation, wherein the process operations include adjusting the speed, heating and longitudinal and transverse stretching of the strip.

11. The device as claimed in claim 7, wherein said measuring means includes:
  a light-sensitive detector for converting an image of the portion of the transilluminated strip into electrical signals;
  means, connected to said light-sensitive detector, responsive to the electrical signals for comparing the electrical signals with a threshold value indicative of a material that is unchanged with respect to thickness and molecule chain orientation, wherein differences between the electrical signals and the threshold value are indicative of changes in thickness and molecule chain orientation in the strip.

12. The device as claimed in claim 11, further including:
  a polychromatic light source; and
  a diffuser screen terminating said light source.

13. The device as claimed in claim 12, wherein said light source, said diffuser screen and said first polarizing means are arranged on one side of the strip and said second polarizing means and said comparing means are arranged on the other side of the strip.

14. The device as claimed in claim 11, wherein a filter is placed between the portion of the transilluminated strip and said light-sensitive detector, said filter suppressing interferences caused by slight intensity variations in a background area of said strip.

15. The device as claimed in claim 11, wherein wherein said imaging elements comprise diodes.

* * * * *